US012576178B2

(12) United States Patent
Kim

(10) Patent No.: US 12,576,178 B2
(45) Date of Patent: Mar. 17, 2026

(54) APPARATUS FOR PROCESSING ARTIFICIAL TOOTH WITH DISINFECTION AND STERILIZATION FUNCTION

(71) Applicant: ZEUS TECH CO., LTD., Gangwon-do (KR)

(72) Inventor: Hong Youn Kim, Gangwon-do (KR)

(73) Assignee: ZEUS TECH CO., LTD., Gangwon-do (KR)

( * ) Notice: Subject to any disclaimer, the term of this patent is extended or adjusted under 35 U.S.C. 154(b) by 564 days.

(21) Appl. No.: 17/993,914

(22) Filed: Nov. 24, 2022

(65) Prior Publication Data

US 2023/0302185 A1      Sep. 28, 2023

(30) Foreign Application Priority Data

Mar. 25, 2022    (KR) ........................ 10-2022-0037544

(51) Int. Cl.
| | |
|---|---|
| *A61L 9/14* | (2006.01) |
| *A61C 8/00* | (2006.01) |
| *A61C 13/08* | (2006.01) |
| *A61K 6/816* | (2020.01) |
| *A61K 6/818* | (2020.01) |
| *A61L 2/18* | (2006.01) |
| *A61L 2/22* | (2006.01) |
| *A61L 9/20* | (2006.01) |

(52) U.S. Cl.
CPC .............. *A61L 9/14* (2013.01); *A61C 8/0087* (2013.01); *A61L 9/20* (2013.01); *A61C 13/08* (2013.01); *A61K 6/816* (2020.01); *A61K 6/818* (2020.01); *A61L 2/18* (2013.01); *A61L 2/22* (2013.01)

(58) Field of Classification Search
CPC ...... A61C 8/0087; A61K 6/816; A61K 6/818; A61L 2/10; A61L 2/18; A61L 2202/122
See application file for complete search history.

(56) References Cited

U.S. PATENT DOCUMENTS

| | | | |
|---|---|---|---|
| 6,558,537 B1* | 5/2003 | Herrington | ............ B01D 65/08 |
| | | | 210/323.1 |
| 2018/0353271 A1* | 12/2018 | Steger | ................ B23Q 11/0891 |
| 2019/0099509 A1* | 4/2019 | Martz | ........................ A61L 2/24 |

FOREIGN PATENT DOCUMENTS

| | | | | |
|---|---|---|---|---|
| CN | 209851405 U | * | 12/2019 | |
| KR | 101854730 B1 | * | 5/2018 | ............. B23Q 17/20 |
| KR | 102333676 B1 | * | 12/2021 | ............... A61L 2/24 |
| WO | WO-2021214621 A1 | * | 10/2021 | ........... B23K 37/006 |

* cited by examiner

*Primary Examiner* — Maris R Kessel
*Assistant Examiner* — Eric Talbert
(74) *Attorney, Agent, or Firm* — Revolution IP, PLLC

(57) ABSTRACT

An apparatus for processing an artificial tooth with a disinfection and sterilization function includes: a work bed unit in which a tooth mother material selected from a titanium material or a zirconia material is installed and fixed, and in which a wet-type die that processes a titanium material and a dry-type die that processes a zirconia material are separately disposed; a processing tool unit that has a driving spindle to which a processing tool is coupled at an end thereof and that processes the tooth mother material while moving close to or away from the tooth mother material; and a disinfection/sterilization module that is coupled in a detachable type in the work bed unit and can simultaneously reduce powder and perform disinfection.

3 Claims, 4 Drawing Sheets

600

800

700

710

900

610

700

APPARATUS FOR PROCESSING ARTIFICIAL TOOTH WITH DISINFECTION AND STERILIZATION FUNCTION

CROSS REFERENCE TO RELATED APPLICATION

The present application claims priority to Korean Patent Application No. 10-2022-0037544, filed Mar. 25, 2022, the entire contents of which is incorporated herein for all purposes by this reference.

BACKGROUND OF THE INVENTION

Field of the Invention

The present disclosure relates to an apparatus for processing an artificial tooth with a disinfection and sterilization function, in more detail, an apparatus for processing an artificial tooth with a disinfection and sterilization function, the apparatus being able to perform sterilization while reducing powder that is produced in the process of machining an artificial tooth.

Description of the Related Art

A dental medical device is used to prevent, diagnose, and treat diseases or abnormalities of the maxillofacial region, including teeth, surrounding tissues, and the oral cavity. Notably, dental materials constitute a significant portion of medical devices, often warranting specific designation.

As a dental processing apparatus, particularly, a tooth processing apparatus, various kinds of processing apparatus such as a tuning or machining center, or a CNC lathe have been developed, and the most important thing for these tooth processing apparatus is that although mechanical properties such as strength of an artificial tooth is important, processing precision and complication for reducing a sense of difference by minimizing a processing error.

However, dust or powder is remarkably produced in this processing process, so the powder contaminates the work environment, injures workers' health, and provides a reason of environmental contamination, and the particles of powder are very small, so there is a problem that powder piles up on other devices.

Further, there is a problem that there is a high possibility of bacilli infection due to the workers' hands, etc. in a processing process, which has adverse influence on the yield of artificial tooth products.

SUMMARY OF THE INVENTION

The present disclosure has been made in an effort to solve the problems described above and provides an apparatus for processing an artificial tooth with a disinfection and sterilization function, the apparatus being able to remarkably suppress production of dust or powder, remove a reason of environmental contamination, and minimize piling-up on other devices through a disinfection water producer, an air purifier, and a UV lamp in a work bed unit, and being able to reduce the possibility of infection due to worker's hands and correspondingly improve a yield of artificial teeth because disinfection water is sprayed and ultraviolet light is emitted in a processing process.

In order to achieve the objectives, an apparatus for processing an artificial tooth with a disinfection and sterilization function according to the present disclosure may include: a work bed unit in which a tooth mother material selected from a titanium material or a zirconia material is installed and fixed, and in which a wet-type die that processes a titanium material and a dry-type die that processes a zirconia material are separately disposed; a processing tool unit that has a driving spindle to which a processing tool is coupled at an end thereof and that processes the tooth mother material while moving close to or away from the tooth mother material; and a disinfection/sterilization module that is coupled in a detachable type in the work bed unit and can simultaneously reduce powder and perform disinfection.

The disinfection/sterilization module may include: a casing that has a lower spray nozzle; a UV lamp disposed on a bottom inside the casing; a disinfection water producer producing and spraying disinfection water to the tooth mother material using tap water; and an air purifier suctioning and filtering the powder.

The air purifier may include: a sleeve body; a suction fan rotatably disposed in the sleeve body; a HEPA air filter being able to filter out powder and bacteria; and a driving unit driving the suction fan.

The disinfection water producer may include: a storage tub in which tap water is stored; an electrolyzation module including a positive charge portion and a negative charge portion that are plated with iridium; and a production body connected to the electrolyzation module.

The production body may have: an LCD window and a production completion information button; and a function switch and a USB terminal.

The production body may have a pH detection sensor measuring a pH value and a TDS sensor measuring a TDS value.

A pH value, a TDS value, and a tap water amount may be displayed on the LC window.

The apparatus for processing an artificial tooth with a disinfection and sterilization function according to the present disclosure can remarkably suppress production of dust or powder, remove a reason of environmental contamination, and minimize piling-up on other devices through a disinfection water producer, an air purifier, and a UV lamp in a work bed unit, and being able to reduce the possibility of infection due to worker's hands and correspondingly improve a yield of artificial teeth because disinfection water is sprayed and ultraviolet light is emitted in a processing process.

BRIEF DESCRIPTION OF THE DRAWINGS

The above and other objectives, features and other advantages of the present invention will be more clearly understood from the following detailed description when taken in conjunction with the accompanying drawings, in which.

DETAILED DESCRIPTION OF THE INVENTION

Hereafter, an apparatus for processing an artificial tooth with a disinfection and sterilization function according to an embodiment of the present disclosure is described in detail with reference to the accompanying drawings.

Figure 1:
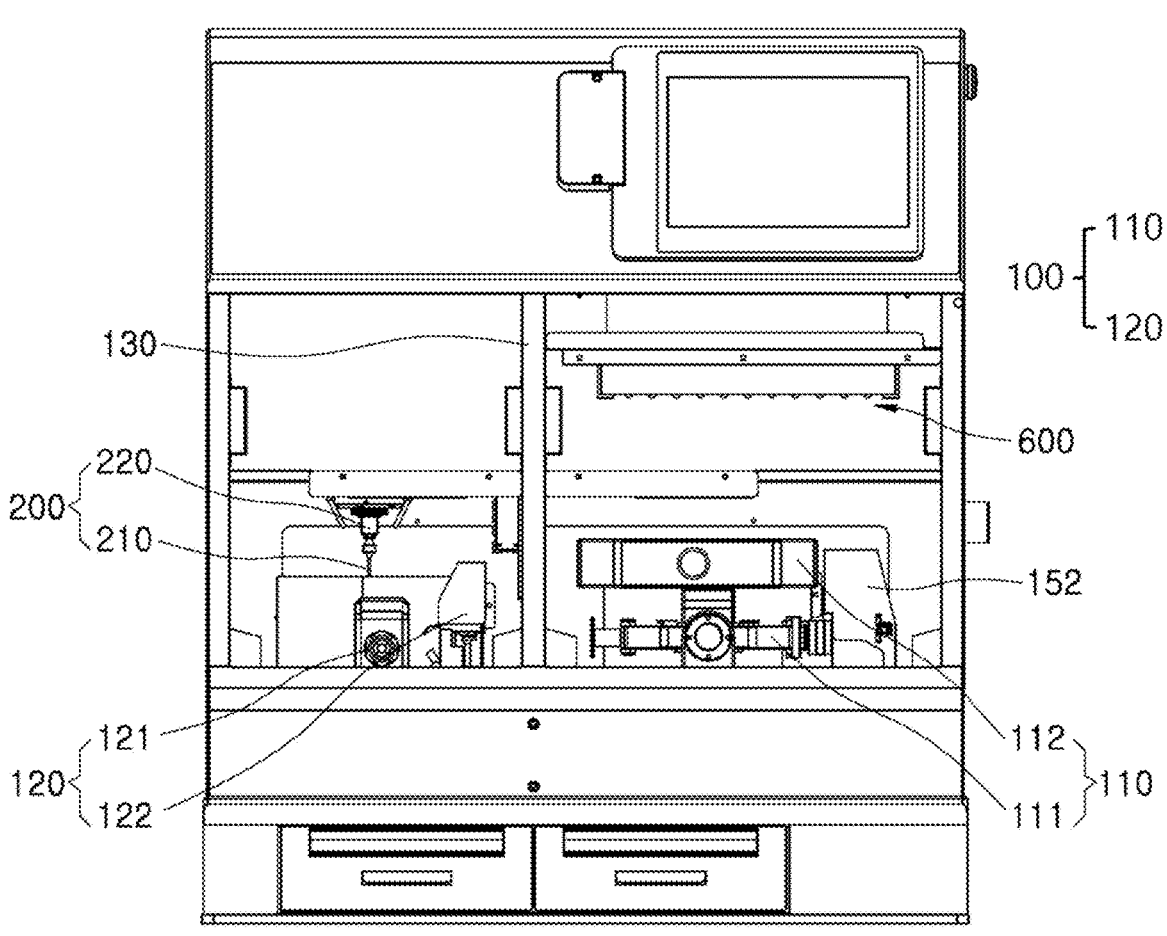
FIG. 1 is a front view of an apparatus for processing an artificial tooth with a disinfection and sterilization function according to an embodiment of the present disclosure.
Figure 2:
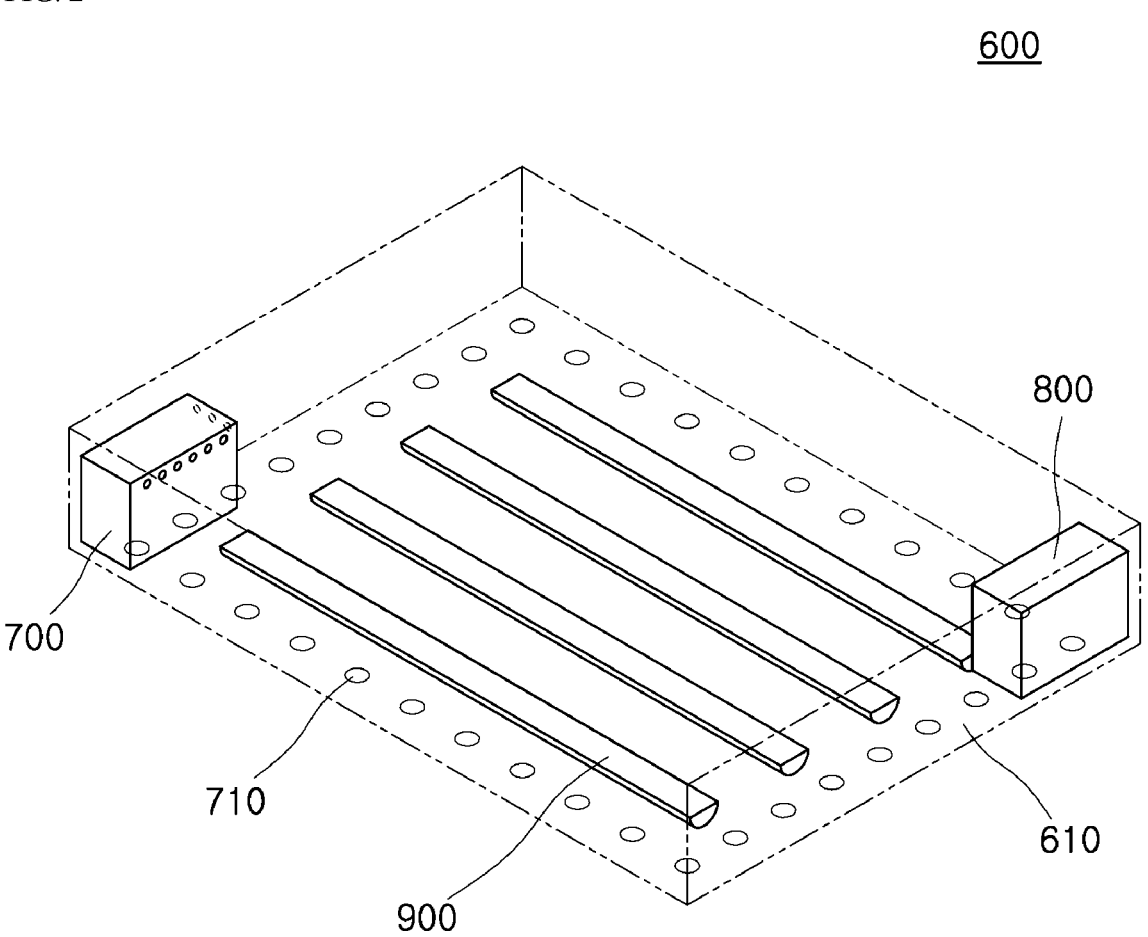
FIG. 2 is a schematic perspective view of a disinfection/sterilization module according to an embodiment of the present disclosure.
Figure 3:
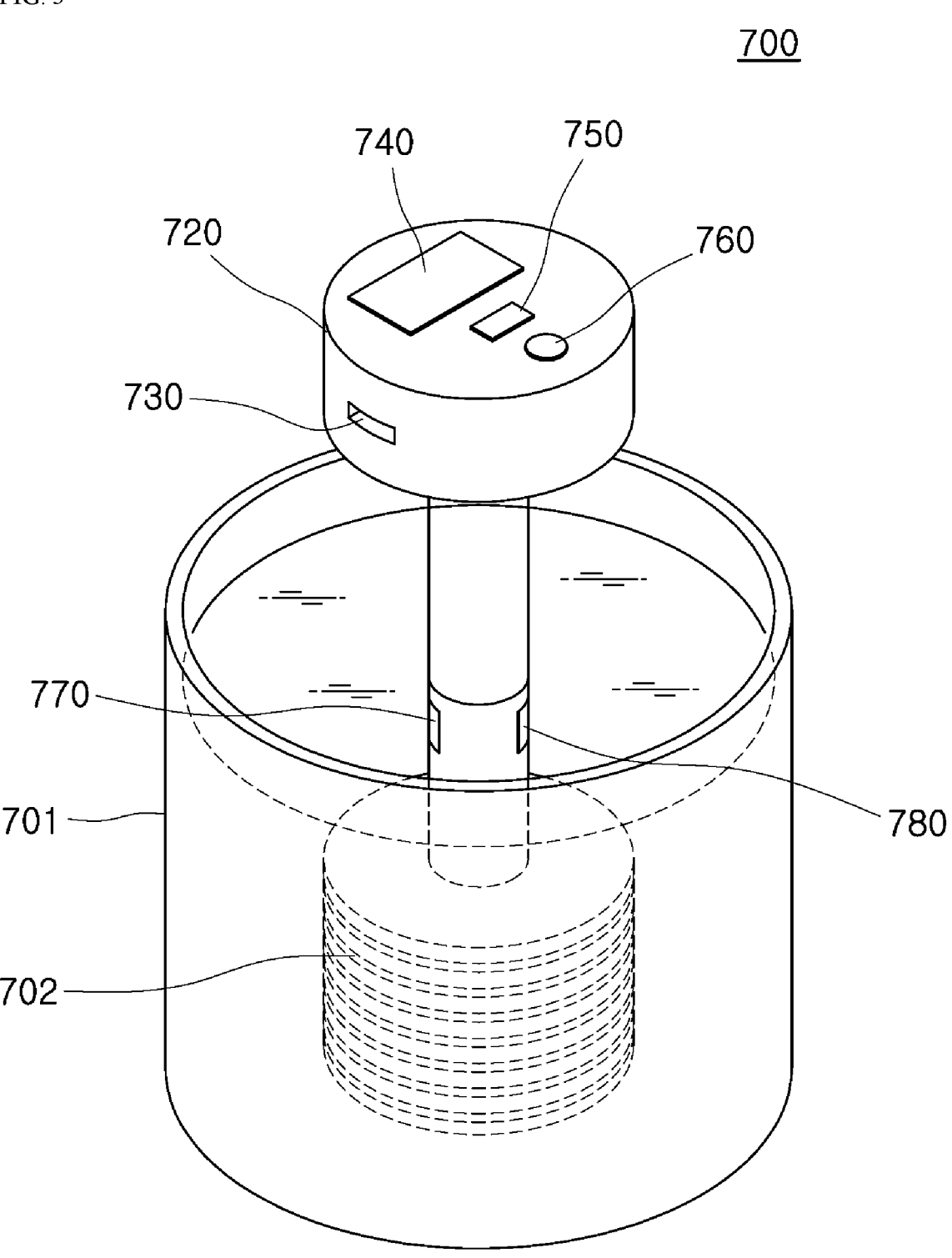
FIG. 3 is a schematic perspective view of a disinfection water producer of the disinfection/sterilization module according to an embodiment of the present disclosure.
Figure 4:
FIG. 4 is a schematic perspective view of an air purifier of the disinfection/sterilization module according to an embodiment of the present disclosure.

FIG. 1 is a front view of an apparatus for processing an artificial tooth with a disinfection and sterilization function according to an embodiment of the present disclosure, FIG. 2 is a schematic perspective view of a disinfection/sterilization module according to an embodiment of the present disclosure, FIG. 3 is a schematic perspective view of a disinfection water producer of the disinfection/sterilization module according to an embodiment of the present disclosure, and FIG. 4 is a schematic perspective view of an air purifier of the disinfection/sterilization module according to an embodiment of the present disclosure.

An apparatus 100 for processing an artificial tooth with a disinfection and sterilization function according to the present disclosure, as shown in FIGS. 1 to 4, may include: a work bed unit 100 in which a tooth mother material selected from a titanium material or a zirconia material is installed and fixed, and in which a wet-type die 120 that processes a titanium material and a dry-type die 110 that processes a zirconia material are separately disposed; a processing tool unit that has a driving spindle 220 to which a processing tool 210 is coupled at an end thereof and that processes the tooth mother material while moving close to or away from the tooth mother material; and a disinfection/sterilization module that is coupled in a detachable type in the work bed unit and can simultaneously reduce powder and perform disinfection.

The wet-type die 120 and the dry-type die 110 may be separately disposed at the left and right, respectively, on the work bed unit 100, mainly as shown in FIGS. 1 to 3. A central partition wall 130 is disposed between the wet-type die 120 and the dry-type die 110, and a through-hole (not shown) through which the processing tool unit 200 is conveyed without interference may be formed in the central partition wall 130.

The wet-type die 120 has a wet-type jig 121, a driving unit, and a pickup station 122, and a titanium material that should be cut with cutting oil may be processed on the wet-type die 120. In this case, the titanium material may be processed into a tooth mother material of an abutment that is coupled to the bottom of an artificial tooth.

Further, the dry-type die 110 is disposed at the right side in FIG. 1 and may have a first dry-type jig 111 that can rotate on a b axis (about a y axis), a driving unit, a second dry-type jig 112 that can rotate on an a axis (about an x axis) disposed perpendicular to the b axis, and a driving unit 152. The first dry-type jig 111 and the second dry-type jig 112 interact with each other, whereby an artificial tooth can be processed, and a separate fixing assembly (not shown) that fixes a tooth mother material may be coupled to the first dry-type jig 111. A zirconia material that is a material of an artificial tooth may be usually processed on the dry-type die 110.

A powder collector is disposed under the dry-type die 110, so it is possible to suction downward powder and chips.

Describing the work bed unit 100 in more detail, a processing environment should be changed in accordance with the levels of difficult-to-cut materials, so a titanium material is processed on the dry-type die and a zirconia material is processed on the wet-type die, whereby simultaneous processing may be possible.

By simultaneously processing various materials in this way, the apparatus can be operated continuously rather than discontinuously, and additional processes are omitted and processing is possible through a single process, so productivity can be improved.

Meanwhile, there is a problem that dust or powder is remarkably produced in a processing process, whereby such powder contaminates a work environment and injures workers' health.

Accordingly, in the present embodiment, a disinfection/sterilization module 600 may be disposed in the work bed unit 100. The disinfection/sterilization module is provided in a module type and an be coupled in a detachable type in the work bed 100.

The disinfection/sterilization module 600 may include: a casing 610 that has a lower spray nozzle 710; a UV lamp 900 disposed on the bottom inside the casing 610; a disinfection water producer 700 producing and spraying disinfection water to the tooth mother material using tap water; and an air purifier 800 suctioning and filtering the powder.

The lower spray nozzle 710 may be disposed at the lower portion of the casing 610.

The UV lamp 900 may be disposed at the center portion of the casing 610 and ultraviolet light can sterilize a tooth mother material and internal air in the work bed unit 100 through the UV lamp 900.

The disinfection water producer 700 and the air purifier 800 may be disposed in the casing 610.

The air purifier 800 may include: a sleeve body 810; a suction fan 820 that is rotatably disposed in the sleeve body 801; a hepa/air filter 840 that can filter out powder and bacteria; and a driving unit 830 that drives the suction fan 820.

Anaerobic bacilli such a power or bacteria in the air suctioned through a suction hole 850 by the suction fan 820 are filtered out through the hepa/air filter 840, and the purified air is discharged to the outside through a discharge hole 860. In this case, the outside may be the inside of the casing 610.

The disinfection water producer 700 is a component that produces and sprays disinfection water to the tooth mother material using tap water. To this end, the disinfection water producer 700, referring to FIG. 2, usually may include a storage tub 701 in which tap water is stored; an electrolyzation module 702 including positive charge portion and a negative charge portion that are plated with iridium; and a production body 720 that is connected to the electrolyzation module 702.

Tap water may be stored in the storage tub 701.

The electrolyzation module 702 is a module that produces sodium hypochlorite and hypochlorous acid disinfection water at a level of 30 ppm~50 ppm by electrolyzing chlorine in tap water. In detail, when electrolysis is performed with salt, sodium hypochlorite is produced, and tap water can be disinfection water of hypochlorous acid.

The production body 720 may have an LCD window 740, a production completion information button 760, a function switch 750, and a USB terminal 730.

Further, the a pH detection sensor 770 and a TDS sensor 780 may be disposed in a bar connecting the production body 720 and the electrolyzation module 702.

A pH value, a TDS value (total dissolved solid), and a tap water amount can be displayed on the LC window 740.

The electrolyzation module may be driven to correspond to a pH value and a TDS value stored in advance in accordance with the amount of tap water.

The production completion information button 760 can emit red light during electrolysis and can emit blue light when electrolysis is finished. For example, when the density of disinfection water reaches 30 ppm, blue light is emitted.

Meanwhile, the disinfection/sterilization module 600 is provided in a module type, so it can be freely attached/detached and can be used not only for an apparatus for processing a tooth, but for other purposes.

As described above, generation of dust or powder can be remarkably suppressed, a reason of environmental contamination can be removed, and piling-up on other devices can be minimized by the disinfection water producer 700, the air purifier 800, and the UV lamp 900 in the work bed unit 100. Further, disinfection water is sprayed and ultraviolet light is radiated in a processing process, so it is possible to reduce a possibility of bacilli infection due to the workers' hands, etc. and correspondingly improve the yield of artificial tooth products.

The processing tool unit 200, mainly as shown in FIGS. 1 and 2, has a processing tool 210 at the front end and the processing tool 210 can be coupled on a driving spindle 220. The driving spindle 220 can be coupled to be rotatable by a driving motor 240 supported on a spindle bracket.

As described above, generation of dust or powder can be remarkably suppressed, a reason of environmental contamination can be removed, and piling-up on other devices can be minimized by the disinfection water producer 700, the air purifier 800, and the UV lamp 900 in the work bed unit 100 having this configuration. Further, disinfection water is sprayed and ultraviolet light is radiated in a processing process, so it is possible to reduce a possibility of bacilli infection due to the workers' hands, etc. and correspondingly improve the yield of artificial tooth products.

Further, in a rest time before/after processing or times without people, automatic sterilization and air purification functions are performed, so a disinfection and sterilization function may be performed.

Although the present disclosure was described above in detail by means of embodiments, the present disclosure is not limited to the specific embodiments and should be construed on the basis of claims. Further, it should be understood that the present disclosure may be changed and modified in various ways by those skilled in the art without departing from the scope of the present disclosure.

What is claimed is:

1. An apparatus for processing an artificial tooth with a disinfection and sterilization function, the apparatus comprising:

a work bed unit configured to hold a tooth material, the tooth material being selected from the group consisting of a titanium material and a zirconia material, wherein a wet-type die for processing the titanium material and a dry-type die for processing zirconia material are separately disposed in the work bed unit;

a processing tool unit including a driving spindle and a processing tool coupled at an end of the driving spindle the processing tool unit being configured to move toward or away from the tooth material to machine the tooth material; and a disinfection and sterilization module detachably coupled to the work bed unit and configured to simultaneously reduce a powder and perform disinfection, wherein the disinfection and sterilization module includes:

a casing having a lower spray nozzle;

a UV lamp disposed a a bottom inside the casing;

a disinfection water producer including a storage tub for storing tap water, an electrolyzation module including a positive charge portion and a negative charge portion each plated with iridium, and a production body connected to the electrolyzation module; and an air purifier including a sleeve body, a suction fan rotatably disposed in the sleeve body, a HEPA air filter configured to filter out powder and bacteria, and a driving unit configured to drive the suction fan, wherein the disinfection and sterilization module is configured to operate concurrently with the processing tool unit during machining of the tooth material such that powder generated during a machining process is reduced and the tooth material is disinfected by spraying hypochlorous acid disinfection water having a concentration of 30 ppm to 50 ppm and by emitting ultraviolet light onto the tooth material during the machining process.

2. The apparatus of claim 1, wherein the production body has an LCD window, and a production completion information button, and a function switch, and a USB terminal.

3. The apparatus of claim 2, wherein the production body has a pH detection sensor configured to measure a pH value and a TDS sensor configured to measure a TDS value.

* * * * *